US011511136B2

(12) United States Patent
Dilmanian (10) Patent No.: US 11,511,136 B2
(45) Date of Patent: Nov. 29, 2022

(54) METHOD FOR TREATING DAMAGED PERIPHERAL NERVES USING X-RAY MICROBEAM IRRADIATION

(71) Applicant: THE RESEARCH FOUNDATION FOR STATE UNIVERSITY OF NY, Albany, NY (US)

(72) Inventor: F. Avraham Dilmanian, Great Neck, NY (US)

(73) Assignee: The Research Foundation for the State University of New York, Albany, NY (US)

( * ) Notice: Subject to any disclaimer, the term of this patent is extended or adjusted under 35 U.S.C. 154(b) by 160 days.

(21) Appl. No.: 16/764,362

(22) PCT Filed: Nov. 16, 2018

(86) PCT No.: PCT/US2018/061619
§ 371 (c)(1),
(2) Date: May 14, 2020

(87) PCT Pub. No.: WO2019/099902
PCT Pub. Date: May 23, 2019

(65) Prior Publication Data
US 2020/0276457 A1   Sep. 3, 2020

Related U.S. Application Data

(60) Provisional application No. 62/587,848, filed on Nov. 17, 2017.

(51) Int. Cl.
*A61N 5/10* (2006.01)
*A61K 35/30* (2015.01)

(52) U.S. Cl.
CPC ............ *A61N 5/1084* (2013.01); *A61K 35/30* (2013.01); *A61N 5/1045* (2013.01); *A61N 5/1081* (2013.01); *A61N 2005/1091* (2013.01)

(58) Field of Classification Search
CPC .. A61N 5/1084; A61N 5/1045; A61N 5/1081; A61N 5/10; A61N 2005/1091; A61K 35/30
See application file for complete search history.

(56) References Cited

U.S. PATENT DOCUMENTS 1,115,475 A   10/1914   Saltzman
5,339,347 A   8/1994   Slatkin et al.
(Continued)

FOREIGN PATENT DOCUMENTS

AU   2013203088 A1   9/2013
AU   2019202401 B2   5/2019
(Continued)

OTHER PUBLICATIONS

ISA/US, International Search Report for PCT/US18/61619, dated Feb. 5, 2019.
(Continued)

*Primary Examiner* — Kaylee R Wilson
(74) *Attorney, Agent, or Firm* — Betsy Kingsbury Dowd, Esq; BKDowd Law, P.C.

(57) ABSTRACT

A method for treating damaged peripheral nerves of a subject includes irradiating at least a portion of the damaged PNs with an array of x-ray microbeams having an in-beam dose sufficient to at least initiate demyelination, each of the microbeams being no greater than 0.7 mm in thickness, and separated for tissue sparing, e.g., by at least 0.05 mm, and optionally administering schwann cell progenitors (SCPs) to the irradiated portion to remyelination before or after irradiating. In-beam dose may be between about 30 to 200 Gy. The method may include irradiating using an x-ray tube of a CT scanner having a multi-aperture collimator mounted thereto and on/near the subject. The SCPs may be adult rat olfactory sphere cells or neural stem cells.

30 Claims, 6 Drawing Sheets

(56) References Cited

U.S. PATENT DOCUMENTS

| | | | |
|---|---|---|---|
| 6,494,900 | B1 | 12/2002 | Salansky |
| 7,544,171 | B2 | 6/2009 | Schaden et al. |
| 7,746,979 | B2 | 6/2010 | Dilmanian et al. |
| 8,475,506 | B1 | 7/2013 | Bendett |
| 9,950,189 | B1 | 4/2018 | Morries |
| 10,589,120 | B1 | 3/2020 | Bellinger |
| 10,905,897 | B2 | 2/2021 | Morries |
| 2003/0076927 | A1 | 4/2003 | Nakashima et al. |
| 2007/0165778 | A1 | 7/2007 | Dilmanian et al. |
| 2008/0192892 | A1* | 8/2008 | Dilmanian ............ A61N 5/1045 378/65 |
| 2008/0292052 | A1 | 11/2008 | Dilmanian et al. |
| 2009/0093863 | A1* | 4/2009 | Dilmanian ............. G21K 1/046 607/88 |
| 2009/0136463 | A1 | 5/2009 | Bunge et al. |
| 2009/0317439 | A1* | 12/2009 | Turzi ..................... A61K 35/39 435/308.1 |
| 2010/0074409 | A1 | 3/2010 | John et al. |
| 2011/0092781 | A1 | 4/2011 | Gertner |
| 2011/0092880 | A1 | 4/2011 | Gertner |
| 2013/0066237 | A1 | 3/2013 | Smotrich |
| 2014/0119496 | A1 | 5/2014 | Zhou |
| 2014/0194786 | A1 | 7/2014 | Gertner et al. |
| 2015/0094516 | A1* | 4/2015 | Taguchi .................... G06T 7/74 382/103 |
| 2015/0140009 | A1 | 5/2015 | Goukassian |
| 2016/0296764 | A1 | 10/2016 | Bellinger |

FOREIGN PATENT DOCUMENTS

| | | | |
|---|---|---|---|
| CN | 201368856 Y | 12/2009 | |
| CN | 101927065 A | 12/2010 | |
| CN | 107684668 B | 4/2020 | |
| EP | 2077901 A2 | 7/2009 | |
| EP | 3005944 A1 | 4/2016 | |
| EP | 2830645 B1 | 8/2017 | |
| EP | 2938399 B1 | 4/2020 | |
| WO | WO9203536 A1 | 3/1992 | |
| WO | 2006086631 A2 | 8/2006 | |
| WO | 2008124801 A2 | 10/2008 | |
| WO | 2009117323 A2 | 9/2009 | |
| WO | 2011046879 A1 | 4/2011 | |
| WO | 2012098548 A1 | 7/2012 | |
| WO | 2014066853 A | 5/2014 | |
| WO | WO-2017147491 A1 * | 8/2017 | ............. A61K 35/30 |
| WO | WO-2018090006 A1 * | 5/2018 | ............. A61K 35/28 |
| WO | 2020185897 A1 | 9/2020 | |

OTHER PUBLICATIONS

Dilmanian F.A., Qu Y., Feinendegen L.E., Pena L.A., Bacarian T., Henn F.A., Kalef-Ezra J., Liu S., Zhong Z., McDonald J.W. Tissue-sparing effect of x-ray microplanar beams particularly in the CNS: Is a bystander effect involved?. Experimental Hematology 2007; 35: 69-77.

Laissue J.A., Blattmann J., Wagner H.P., Grotzer M.A., Slatkin D.N. Prospects for microbeam radiation therapy of brain tumors in children to reduce neurological sequelae. Developmental Medicin & Child Neurology. 2007; 49: 577-581.

Serduc R, Verant P, Vial JC, Farion R, Rocas L, Remy C, Fadlallah T, Brauer E, Bravin A, Laissue J, B:Atmann H, Van Der Sanden B. In vivo two-photon microscopy study of short-term effects of microbeam irradiation on normal mouse brain microvasculature. Int J Radiat Oncol Biol Phys. 2006;64(5):1519-27.

Klein D., Martini R. Myelin and macrophages in the PNS: An intimate relationship in trauma and disease. Brain Research. 2016; 1641: 130-138.

Goldman S.A. Disease targets and strategies for the therapeutic modulation of endogenous neural stem and progenitor cells. Clinical Pharmacology and Therapeutics. 2007: 82(4); 453-460.

Woodhoo, A., et al., Schwann cell precursors: a favourable cell for myelin repair in the Central Nervous System. Brain (2007): 130, 2175-2185.

Bercury, K.K., et al., Dynamics and mechanisms of CNS myelination. Dev. Cell. 2015; 32(4):447-58.

Ohnishi, Y., et al., Adult olfactory sphere cells are a source of oligodendrocyte and Schwann cell progenitors. Stem Cell Res. (2013): 11(3):1178-90.

Lehoczky, J.A., Digit Tip Regeneration and Beyond: Schwann Cell Progenitors to the Rescue. Cell Stem Cell. Oct. 6, 2016;19(4):417-418.

Svennigsen, A. F, Dahlin, L. B. Repair of the Peripheral Nerve—Remylination that Works. Brain Sci. (2013): 3, 1182-1197.

Krause, M., et al., Direct Genesis of Functional Rodent and Human Schwann Cells from Skin Mesenchymal Precursors, Stem Cell Reports. 2014, 3:1, 85-100.

Robinson, S., et al., Contact with central nervous system myelin inhibits oligodendrocyte progenitor maturation. Dev. Biol. Dec. 1, 1999;216(1):359-68.

Slatkin, D.N., et al., Subacute neuropathological effects of microplanar beams of x-rays from a synchrotron wiggler. Proc. Natl. Acad. Sci. U.S.A. 1995;92(19):8783-7.

Dilmanian, F.A., et al., X-ray micro beams: Tumor therapy and central nervous system research. Nucl. Instrum. Methods Phys. Res. A. 2005;548(1-2):30-37.

Monk, K.R., et al., New Insights on Schwann Cell Development. Glia. Aug 2015: 63(8): 1376-1393.

Dilmanian, F.A., et al., Interlaced x-ray microplanar beams: a radiosurgery approach with clinical potential. Proc. Natl. Acad. Sci. U.S.A. 2006;103(25):9709-14.

Liu, G., et al., Genetically modified Schwann cells producing glial cell line-derived neurotrophic factor inhibit neuronal apoptosis in rat spinal cord injury. Molecular Medicine Reports. (2014): 9: 1305-1312.

Kocsis, J.D., et al. Cell transplatation of peripheral-myelin-forming cells to repair the injured spinal cord. Journal of Rehabilitation Research and Development. (2002): 39 (2): 287-298.

Jessen, K.R., Mirsky, R. The repair Schwann cell and its function in regenerating nerves. J Physiol 594.13 (2016): 3521-3531.

Robinson, S., et al.,"Contact with Central Nervous System Myelin Inhibits Oligodendrocyte Progenitor Maturation," Dev. Bio., Jun. 18, 1999, vol. 216:359-368 (1999), Academic Press.

* cited by examiner

METHOD FOR TREATING DAMAGED PERIPHERAL NERVES USING X-RAY MICROBEAM IRRADIATION

CROSS-REFERENCE TO RELATED APPLICATIONS

This application is a U.S. national phase filing of Int'l Application Ser. No. PCT/US18/61619, with an international filing date of Nov. 16, 2018, which claims the benefit of and priority to U.S. Provisional Application Ser. No. 62/587,848, filed Nov. 17, 2017 entitled "CAUSING SCHWANN CELL REGENERATION USING X-RAY MICROBEAM IRRADIATION AND ADMINISTERING SCHWANN-CELL PRECURSOR CELLS TO PRODUCE REMYELINATION IN PERIPHERAL NERVES," the entirety of each of which is hereby incorporated herein by reference thereto.

FIELD OF DISCLOSURE

The present disclosure relates generally to x-ray radiation therapy and particularly to methods of treatment of peripheral nerve damage using x-ray radiation therapy.

BACKGROUND

Mammalian peripheral nerves can be injured by a variety of ways, including by mechanical means, radiation, and damage caused by the immune system. For example, the sciatic nerve can be crushed in an accident, the cranial nerves and the prostate nerve can be injured during radiation therapy treatments when tumors are to be controlled, and the nerves can be damaged by autoimmune-system disorders.

Although some studies have been performed that suggest the use of radiation treatments for repair of the central nervous system (CNS), the peripheral nervous system (PNS) is different from the central nervous system (CNS) in several ways. First, the cells making myelin for the peripheral nerves are the schwann cells, as opposed to the oligodendrocytes, which produce myelin for the axons in our CNS. Second, while our axons are in the midst of the CNS tissues, which are filled with oligodendrocyte precursor cells (OPCs), also known as progenitor glial cells (PGCs), our peripheral nerves have relatively few schwann cell progenitors (also known as schwann cell precursors) around them. This makes the recovery of our peripheral nerves challenging, whether the damage was produced by mechanical means, by radiation, or by other factors.

It is known that in the CNS, the PGCs do not divide as long as they can sense the existence of myelin around them. This effect is called "contact inhibition." However, a mechanical or other injury to the CNS may "break" this contact inhibition, and allow the PGCs to divide, proliferate, and fill the neighboring tissue denuded from myelin. The resulting new cells may then differentiate into mature glial cells and resume their remyelination function. No similar process of demyelination and remyelination is known for schwann cells or schwann cell progenitor cells, like that described above for the CNS.

Further, no methods of treatment for damaged peripheral nerves using x-ray radiation are known.

SUMMARY

Features of the disclosure will become apparent from the following detailed description considered in conjunction with the accompanying drawings. It is to be understood, however, that the drawings are designed as an illustration only and not as a definition of the limits of this disclosure.

The present disclosure is directed to methods for treating damaged peripheral nerves using x-ray microbeam irradiation.

The present disclosure is further directed to a method for treating damaged peripheral nerve(s) of a subject, which includes irradiating at least a portion of the damaged peripheral nerve with an array of x-ray microbeams having an in-beam dose sufficient to initiate demyelination in the peripheral nerve, wherein each of the microbeams in the array is no greater than 0.7 mm in thickness.

In aspects, the method also includes administering schwann cell progenitors to at least the portion of the damaged peripheral nerve irradiated with the array, preferably stimulating production of new myelin in the damaged peripheral nerve. The schwann cell progenitors may be administered, in aspects, prior to the irradiating step, and in other aspects, the schwann cell progenitors may be administered after, and in some aspects, within an hour after the irradiating step.

The method may also include, in aspects, administering schwann cell progenitors to neighboring tissue to the portion irradiated.

The method may further include, in aspects, repeating each of the steps of irradiating the portion and administering the schwann cell progenitors in a number of treatment sessions, each treatment session being separated by a predetermined period of time. In further aspects, the number of treatment sessions is a number sufficient to produce full remyelination.

In some aspects, the predetermined period of time between each treatment session is sufficient to allow a second demyelination to occur between each treatment session.

In any of the methods of the present disclosure including administering schwann cell progenitors, the schwann cell progenitors may originate from a human, or from an animal other than a human. For example, the schwann cell progenitors may be adult rat olfactory sphere cells.

In aspects, the schwann cell progenitors may be neural stem cells.

In aspects of the methods of the present disclosure, the thickness of each of the microbeams in the array may be between about 0.2 mm and about 0.5 mm inclusive and a spacing on-center between adjacent microbeams in the array may be between about 0.7 mm and about 2.0 mm inclusive.

In aspects, a gap of at least 0.05 mm is maintained between adjacent microbeams over the portion irradiated.

In some aspects, a spacing on-center between adjacent microbeams in the array may be between about 1.1 to about 3 times the thickness of a microbeam.

In aspects of the methods of the present disclosure, in-beam dose of each microbeam may be at least 30 Gy.

In aspects of the methods of the present disclosure, in-beam dose of each microbeam may be at least 100 Gy.

In other aspects, the in-beam dose is between about 30 to 200 Gy, inclusive.

In aspects, the array of microbeams is an array of substantially parallel planar microbeams.

In aspects of the method for treating damaged peripheral nerve(s) of a subject, including irradiating at least a portion of the damaged peripheral nerve with an array of parallel planar x-ray microbeams having an in-beam dose sufficient to initiate demyelination in the peripheral nerve, the in-beam dose is sufficient to ablate myelin of the damaged peripheral nerve, the method including ablating bands of old schwann cells and damaged myelin, thereby making space for new myelin.

In aspects of any of the methods of the present disclosure, the method may further include providing the array of x-ray microbeams, including providing an x-ray source directed at the at least the portion of the damaged peripheral nerves and positioning a multi-aperture collimator downstream and in a trajectory of the x-ray source and near or on the subject to generate the array of x-ray microbeams.

In additional aspects, the x-ray source may be a rotating anode x-ray tube or an orthovoltage x-ray tube.

In still additional aspects, the x-ray source is an x-ray tube of a computed tomography (CT) scanner, the method further including providing the computed tomography scanner and positioning the subject and the x-ray source in the computed tomography scanner such that the x-ray source is directed at the at least the portion of the damaged peripheral nerves, the multi-aperture collimator being positioned within the trajectory of the x-ray source and near or on the subject to generate the array of x-ray microbeams.

The present disclosure is also directed to a method for treating damaged peripheral nerve(s) of a subject, the method including irradiating a portion of the damaged peripheral nerves with an array of parallel planar x-ray microbeams to at least initiate, and in aspects, produce demyelination in the peripheral nerve, each microbeam delivering an in-beam dose of between about 30 to 200 Gy, and wherein each of the microbeams in the array is no greater than 0.7 mm in thickness.

In aspects, the method further includes administering schwann cell progenitors to the portion of the damaged peripheral nerves irradiated with the array, thereby stimulating production of new myelin in the damaged peripheral nerves.

In some aspects, the administering step is performed prior to the irradiating step.

In other aspects, the administering step is performed within an hour after the irradiating step.

In any of the methods of the present disclosure, the schwann cell progenitors may be adult rat olfactory sphere cells, or in other aspects, the schwann cell progenitors may be neural stem cells.

The present disclosure is also directed to a method for treating damaged peripheral nerves of a subject, including irradiating a portion of the damaged peripheral nerve with an array of parallel planar x-ray microbeams to at least initiate, and in embodiments, produce demyelination in the peripheral nerve, each microbeam delivering an in-beam dose of between about 30 to 200 Gy, and wherein each of the microbeams in the array is no greater than 0.7 mm in thickness, the method further including providing the array of parallel planar x-ray microbeams, including providing an x-ray source directed at the portion of the damaged peripheral nerves and positioning a multi-slit collimator downstream and in a trajectory of the x-ray source and near or on the subject to generate the array of parallel, planar x-ray microbeams.

In aspects, the x-ray source includes one of a rotating anode x-ray tube and an orthovoltage x-ray tube.

In some aspects, the x-ray source is an x-ray tube of a computed tomography (CT) scanner, the method further including providing the computed tomography scanner and positioning the subject and the x-ray source in the computed tomography scanner such that the x-ray source is directed at the portion of the damaged peripheral nerves, the multi-slit collimator being positioned in the trajectory of the x-ray source and near or on the subject to generate the array of parallel, planar x-ray microbeams.

The method including providing the computed tomography scanner may further include administering schwann cell progenitors to the portion of the damaged peripheral nerve irradiated with the array, thereby stimulating production of new myelin in the damaged peripheral nerves, wherein the administering step may be performed prior to the irradiating step, or within an hour after the irradiating step.

The present disclosure is also directed to a method for treating a damaged peripheral nerve of a subject, which includes irradiating at least a portion of the damaged peripheral nerves with at least one x-ray microbeam, which is no greater than 0.7 mm in thickness to initiate demyelination in the damaged peripheral nerves.

In aspects, the at least one microbeam delivers an in-beam dose of at least 30 Gy.

In aspects, the method further includes administering schwann cell progenitors to at least the portion of the damaged peripheral nerves irradiated with the at least one microbeam. In further aspects, this may stimulate or enhance production of new myelin in the damaged peripheral nerves.

The administering step, in aspects, is performed prior to the irradiating step.

In additional or optional aspects, the administering step is performed after the irradiating step, and in some aspects, within an hour after the irradiating step.

The schwann cell progenitors, in aspects, may be adult rat olfactory sphere cells, and/or neural stem cells.

In particular aspects, the at least one x-ray microbeam is an array of x-ray microbeams.

In still additional aspects, the at least one x-ray microbeam is an array of substantially parallel planar microbeams.

The method, in aspects, may further include providing the array of x-ray microbeams, including providing an x-ray source directed at the portion of the damaged peripheral nerves and positioning a multi-aperture collimator downstream of the x-ray source and near or on the subject to generate the array of x-ray microbeams.

The x-ray source, in aspects, includes one of a rotating anode x-ray tube and an orthovoltage x-ray tube.

In further aspects, the x-ray source is an x-ray tube of a computed tomography (CT) scanner, the method further including providing the computed tomography scanner and positioning the subject and the x-ray source in the computed tomography scanner such that the x-ray source is directed at the portion of the damaged peripheral nerve, the multi-aperture collimator being positioned near or on the subject to generate the array of x-ray microbeams.

In aspects, a gap of at least 0.05 mm is maintained between adjacent microbeams over the portion irradiated.

In addition to the above aspects of the present disclosure, additional aspects, objects, features and advantages will be apparent from the embodiments presented in the following description and in connection with the accompanying drawings.

BRIEF DESCRIPTION OF THE DRAWINGS

The drawings constitute a part of this disclosure and include examples, which may be implemented in various forms. It is to be understood that in some instances, various aspects of the disclosure may be shown exaggerated or enlarged to facilitate understanding. The teaching of the disclosure can be readily understood by considering the detailed description in conjunction with the accompanying drawings, which are briefly described below.

The various aspects of the present disclosure mentioned above are described in further detail with reference to the aforementioned figures and the following detailed description of certain embodiments.

DETAILED DESCRIPTION

The following detailed description of embodiments in the present disclosure are made with reference to the accompanying drawings. It should be apparent to those skilled in the art that the described embodiments provided herein are illustrative only and not limiting, having been presented by way of example only. All features disclosed in this description may be replaced by alternative features serving the same or similar purpose, unless expressly stated otherwise. Therefore, numerous other embodiments of the modifications thereof are contemplated as falling within the scope of the present disclosure as defined herein and equivalents thereto. In the following description, detailed explanations of related well-known functions or features known in the art are omitted to avoid obscuring the embodiments of the disclosure with unnecessary detail.

Throughout the description, where items are described as having, including, or comprising one or more specific components, or where methods are described as having, including, or comprising one or more specific steps, it is contemplated that, additionally, there are items of the present disclosure that consist essentially of, or consist of, the one or more recited components, and that there are methods according to the present disclosure that consist essentially of, or consist of, the one or more recited processing steps.

Figure 1:
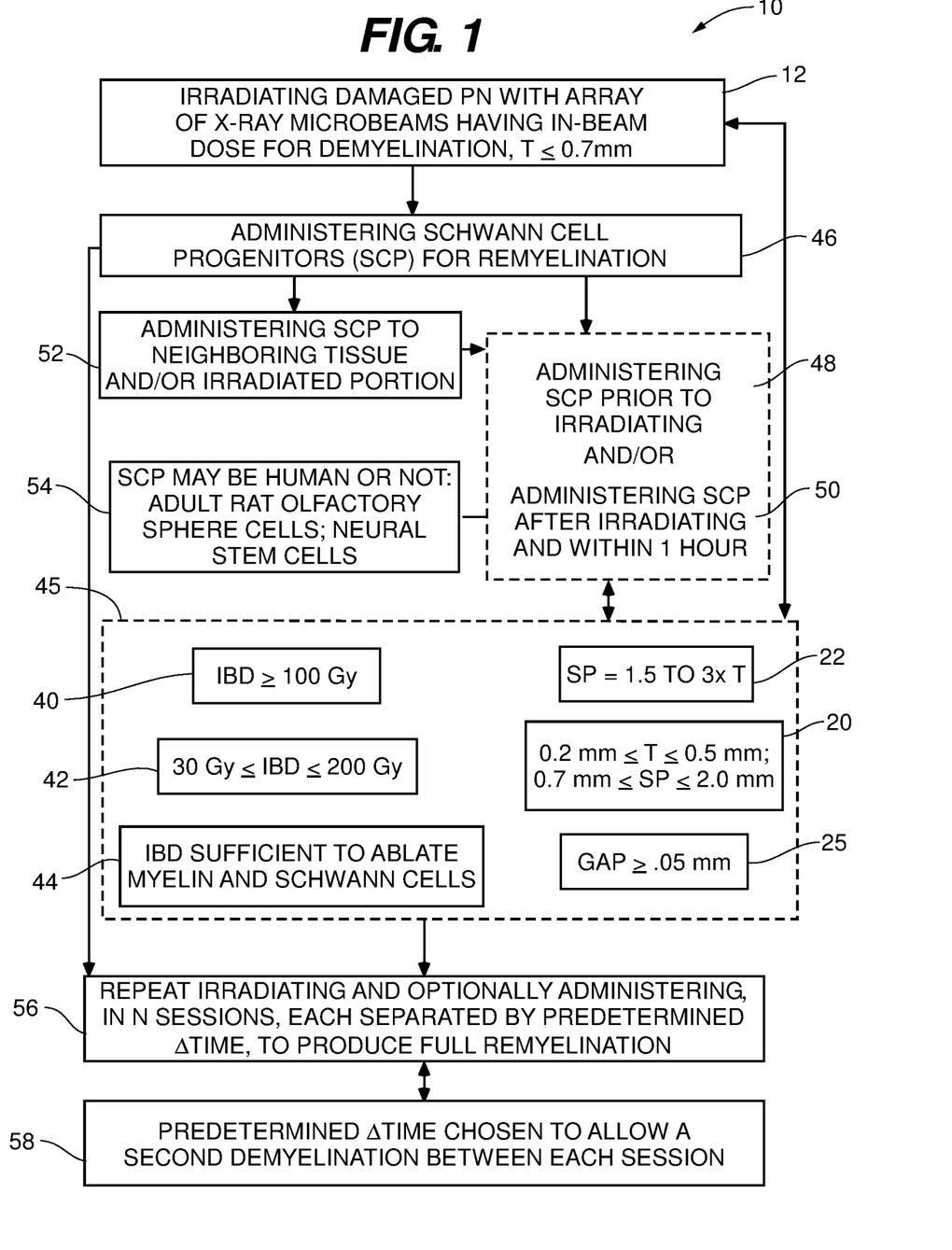
FIG. 1 represents embodiments of methods of the present disclosure for treating peripheral nerve damage of a subject with microbeam x-ray irradiation.

Referring to FIG. 1, the present disclosure is directed to methods 10 for treating damaged peripheral nerves of a subject or patient including irradiating at least a portion of the damaged peripheral nerve(s), at 12, with an array 14 of x-ray microbeams, which may, in embodiments, be parallel or substantially parallel planar microbeams, (see FIG. 2A) having an in-beam dose sufficient to initiate demyelination in the peripheral nerve. Referring to both FIGS. 2A and 2B, each of the microbeams 16 in the array 14 has a thickness 18 that is no greater than 0.7 mm in thickness.

Microbeam arrays of the disclosure also preferably include a spacing on-center 24 (see FIGS. 2A and 2B) sufficient to insure a gap 25 between adjacent microbeams 16 to promote a tissue-sparing effect, as described further below, after irradiation. Referring also to FIG. 1, this gap 25, which may be described as the edge-to-edge spacing between the beams at full-width-half max (FWHM), in embodiments, may be as small as 0.05 mm.

Figure 2A:
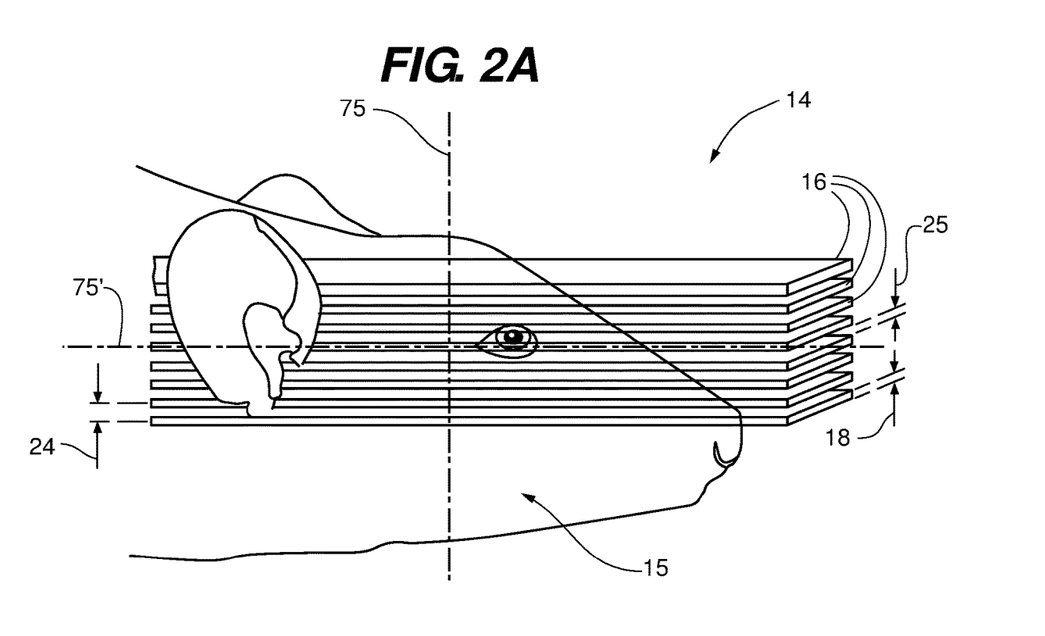
FIG. 2A is a pictorial representation of an array of evenly spaced, parallel, x-ray microbeams irradiating a rat over its head, exemplifying an embodiment of the arrays of microbeams of the present disclosure.

In some embodiments, it may be advantageous to use microbeams 16 that are parallel or substantially parallel planar microbeams, as shown in FIG. 2A, with the microbeams having a rectangular profile in cross-section. However, in embodiments, the array 14 may include microbeams 16 of any shape and arrangement, with the thickness 18 of the microbeams 16 being less than 0.7 mm and with the gap 25 between adjacent microbeams 16 being sufficient to allow tissue-sparing.

Figure 2B:
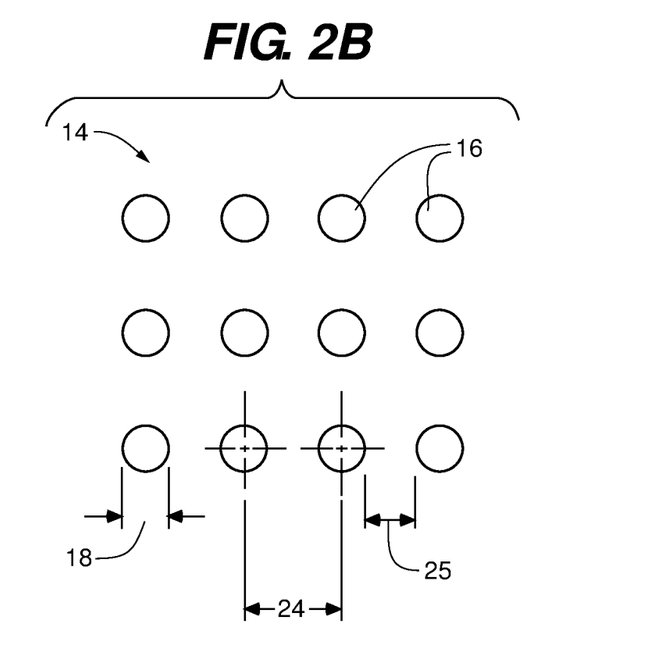
FIG. 2B is a pictorial representation of a cross-section through another embodiment of an array of x-ray microbeams of the disclosure, the microbeams having circular cross-sections.

The array 14 may be a one-dimensional array as shown in FIG. 2A, or a two-dimensional array, as shown in FIG. 2B. While the two-dimensional array of FIG. 2B is set on a rectangular grid with the same gap 25 between adjacent microbeams 16, in embodiments, they could be equally spaced along radii of a circle, or in other embodiments, have no regular pattern of spacing between them. The microbeams 16 in FIG. 2B are of circular cross-section, and are sometimes referred to as pencil beams. As one will appreciate, the microbeams 16 of the disclosure may be in cross-section of any shape, including but not limited to rectangular (planar), square, oval, round or circular, elliptical, polygonal, arched, and so on.

In particular embodiments, the methods 10 include irradiating the portion 32 of the damaged peripheral nerves 30 (see FIG. 3), at 12, with the array 14 characterized, at 20 in FIG. 1, by the thickness 18 of each microbeam being between about 0.2 mm and about 0.5 mm inclusive, and a spacing on-center 24 (see FIGS. 2A, 2B) between adjacent microbeams in the array 14 being between about 0.7 mm and about 2.0 mm inclusive. In further embodiments, the thickness 18 may be between about 0.2 mm and about 0.5 mm inclusive, and the gap 25 between adjacent microbeams 16 is at least 0.05 mm.

As one of skill in the art will appreciate, depending on a focal spot size of the x-ray source generating the microbeams, there will be some amount of divergence in the microbeams. Accordingly, in embodiments, the method includes properly dimensioning a multi-aperture collimator forming the microbeams to account for the natural divergence of the source, such that this gap 25 of at least 0.05 mm is maintained at least over the irradiated portion 32 of the targeted nerves 30.

In any of the embodiments, for example, the methods 10 may include irradiating the portion, at 12, with the array 14 characterized, at 22, in FIG. 1 with the thickness 18 of the microbeams being no greater than 0.7 mm in thickness, and with the gap 25 between the microbeams 16 being sufficient to achieve a tissue-sparing effect. In embodiments, as described above, the gap 25 of at least 0.05 mm is maintained at least over the portion 32 of damaged peripheral nerves 30 being treated. In some further embodiments, the spacing on-center 24 will be at least 1.1 times the thickness 18, or in embodiments, at least 1.2 times the thickness 18, or in embodiments, at least 1.5 times the thickness 18. In further embodiments of any of the methods, the on-center spacing may be between at least 1.5 to 3 (three) times the thickness 18.

The number of beams in the array may be chosen in accordance with the size of the targeted portion of the peripheral nerves for irradiation. In some cases, the entire region of the damaged peripheral nerves can be irradiated with a single array in a single irradiation. In other embodiments, several irradiations may be performed of different portions of the damaged peripheral nerves overall several irradiations to treat the entire region of damaged peripheral nerves. Other irradiation parameters of the array of parallel microbeams will depend on the required in-beam dose and other factors, but the thickness of the microbeams should be less than 0.7 mm, and the gap 25 between them should be sufficient to benefit from the tissue-sparing effect as described supra.

In some embodiments, suitable parameters may be chosen from a range of thicknesses from about 0.2 to 0.6 mm microbeams and a range of on-center spacing from about 0.4 to 1.0 mm, with in-beam doses chosen from a range of between about 30 Gy to 200 Gy.

In further regard to the spacing between the microbeams and the thickness of the microbeams of the present disclosure, the methods of treatment of the present disclosure using x-ray microbeam radiation are based on the tissue-sparing effect observed using segmented high energy x-ray beams of thicknesses less than 0.7 mm. Investigations into the use of so-called microbeams as a possible method of radiation therapy occurred using arrays of parallel planar synchrotron x-rays in the early 1990s at the National Synchrotron Light Source (NSLS), Brookhaven National Laboratory (BNL), under the title of microbeam radiation therapy (MRT). Early studies showed, for example, a tissue-sparing effect after a single exposure of the rat cerebellum to an array of parallel, 37 μm planes of synchrotron x-rays, referred to as microbeams, spaced 75 μm on center, at triplet beams of 250 Gy and 1,000 Gy in-beam, in-depth. At three months there was no visible damage when 250-Gy microbeams were used, while the only damage observed with the 1,000-Gy irradiations was the disappearance of the granular cells in the direct path of each microbeam, but without causing general tissue necrosis. This tissue-sparing effect prompted additional research on the subject of the tissue tolerance of x-ray microbeams, first at the NSLS and soon after also at the European Synchrotron Radiation Facility (ESRF) in Grenoble, France.

Although the radiobiological mechanisms of the tissue-sparing effect of these thin segmented beams are still being studied, it is commonly acknowledged that two mechanisms that broadly underlie this tissue-sparing effect are the "dose-volume effect" and the "prompt biological repair effect." The first effect, which refers to the observation that the smaller the target, the larger is its dose tolerance, is known and its effect is not limited to mm or sub-mm beams. The second "prompt biological repair" effect, however, is specific to x-ray beams with sub-mm dimensions and has been explored in animal studies. It is based on observations of the fast repair of capillary blood vessels from microbeam exposure. For example, in experiments with planar synchrotron-generated microbeams of 25 μm at ESRF at several hundreds of Gy incident dose in a mouse cerebellum, it was observed that the capillary blood vessels repaired themselves within 12-24 hours.

In additional studies at the NSLS in the early 2000s with the rat spinal cord and brain, it was observed that x-ray planar microbeams from 0.02 mm to as thick as 0.68 mm still retained much of their CNS-sparing effect. In fact, three out of four rats transaxially irradiated with an array of microbeams at their spinal cord, with on-center spacing of 3 mm and in-beam doses of 400 Gy, survived for a year. Referring to FIG. 2A, rats irradiated over nearly their entire brain 15 (8 mm×12 mm) with microbeams 16 in the array 14 being substantially parallel and planar, 0.68 mm in thickness 18, and spaced 1.32 mm on-center 24, and delivering 170 Gy in-beam dose, showed no sign of neurological deficits over a year. The above study also showed that two 0.68-mm-thick x-ray minibeam arrays aimed at the target from 90° angles, can be interleaved (or interlaced) to produce a solid radiation field at the target. The technique was then used to ablate a 3 mm target in the rat brain with a 120 Gy dose. No significant damage to the surrounding tissues from MRI studies was observed 6 months later.

It is difficult to assign a factor for the quantitative comparison between the tissue tolerance of segmented thin planar, parallel beams of x-ray radiation, i.e., "microbeams," on the one hand, and solid, conventional beams on the other hand. However, the tissue tolerance can be estimated by comparing the results in the above paragraph indicating that the entire rat brain tolerated 170 Gy of 0.68-mm minibeams spaced 1.32 mm on center, to those by other investigators who exposed a large part of the rat brain to 250 kVp x-rays at a single dose fraction of ~21 Gy. The irradiations produced 50% incidence of white matter necrosis in 52 weeks. Considering nearly no radiation effects were observed in the 170-Gy minibeam exposures at the end of one year, it is estimated that the tolerance advantage of arrays of 0.68 mm thick microbeams over solid x-ray beams in the rat brain example was at least a factor of 8:1, and most probably closer to 10:1. From these observations, it is surmised that radiation therapy using an array of microbeams can be used at high incident doses with less probability of damaging the skin and the normal tissues proximal to the target.

Figure 3:
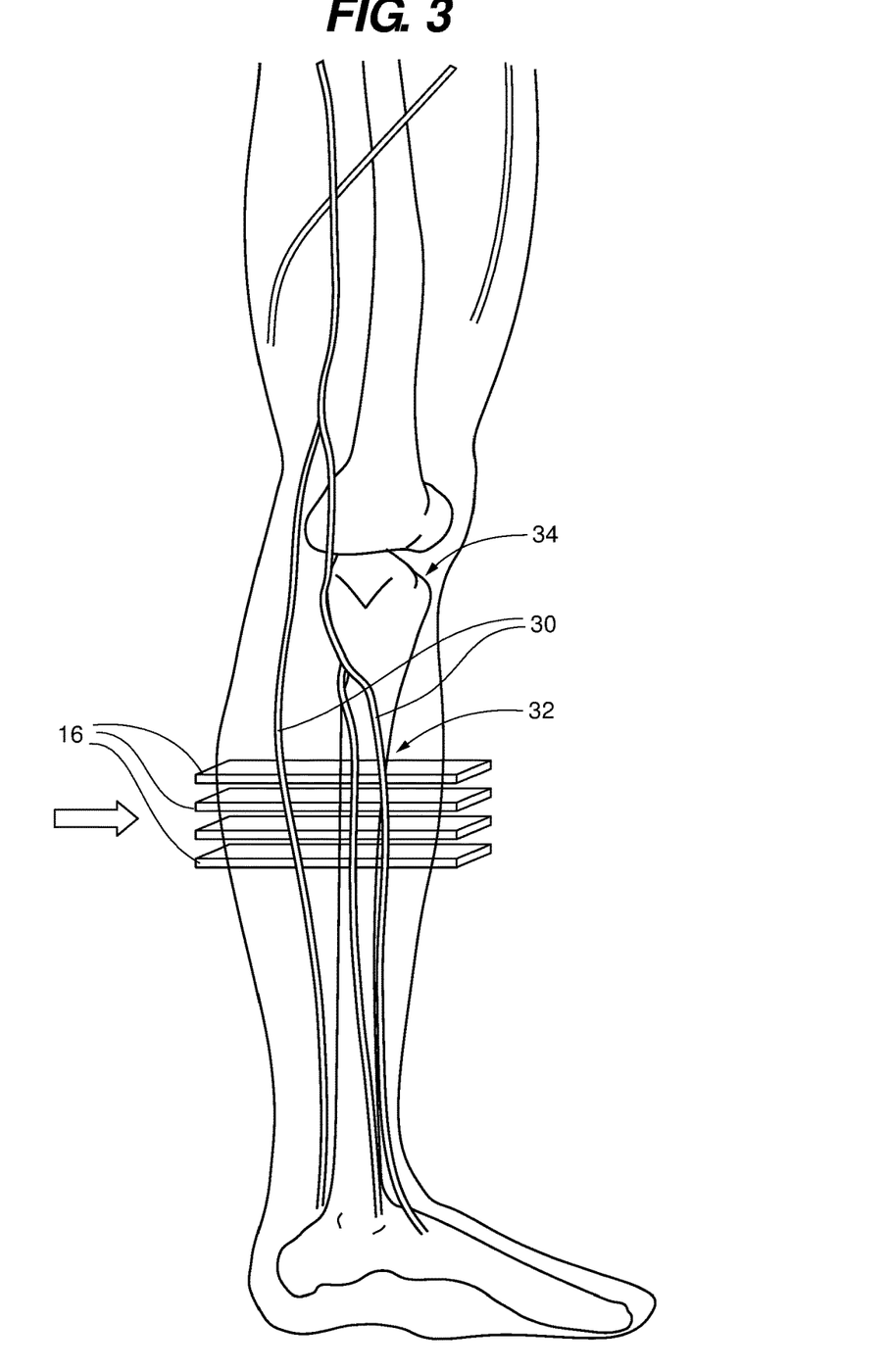
FIG. 3 is a pictorial representation of a portion of several damaged peripheral nerves in a leg being irradiated with an array of microbeams of the disclosure.

Referring again to FIG. 1 as well as to FIG. 3 which shows an array of microbeams 16 irradiating several damaged peripheral nerves 30 of a leg 34, methods for treating damaged peripheral nerves 30 (see FIG. 3) include irradiating at 12, at least a portion 32 of the damaged peripheral nerves 30 with microbeams of a thickness less than 0.7 mm.

It should be appreciated that the volume of tissue targeted for irradiation treatment according to the methods of the present disclosure includes, in embodiments, both the portion 32 of the damaged peripheral nerves 30 targeted for irradiation, and a marginal volume around the damaged peripheral nerves 30. The marginal volume is determined by factors known to those skilled in the art of conventional radiation treatment. Such factors may include the accuracy of the radiation source used to target the damaged peripheral nerves 30, and considerations of possible spreading or misestimation of the extent of the damaged peripheral nerve requiring treatment.

FIG. 3 is a pictorial representation of planar microbeams 16 irradiating the portion 32 of damaged peripheral nerves 30 of a leg 34 requiring treatment.

Referring again to FIGS. 2A and 2B, in any of the embodiments of the methods, the thickness 18 of the microbeams 16 may be about 0.3 mm. The methods of the present disclosure include providing in-beam dose sufficient to initiate demyelination, at 12, and providing the in-beam dose using microbeams of an array 14, which will also facilitate the tissue-sparing and repair effect.

It should be noted that the term "in-beam dose" referred to herein refers to the dose delivered in each microbeam of the array.

In some embodiments, treatment of damaged peripheral nerves by irradiation, at 12, with an array of microbeams of the present disclosure may be sufficient to at least initiate, and in embodiments, produce demyelination with subsequent remyelination. Demyelination with subsequent remyelination may, in embodiments, be achieved in a single irradiation session, or in further embodiments, over more than one session. Determination of a sufficiently high dose for demyelination of a particular peripheral nerve(s) may be determined, in embodiments, through computer models and/or animal studies.

In embodiments, referring to FIG. 1, irradiating a portion 32 of damaged peripheral nerves 30 at sufficiently high doses to at least initiate demyelination, at 12, includes irradiating with in-beam doses of at least 100 Gy in-beam, at 40.

In alternate or additional embodiments, irradiating a portion 32 of damaged peripheral nerves 30 at sufficiently high doses to initiate demyelination, at 12, includes irradiating with in-beam doses in a range of between about 30 Gy and 200 Gy, inclusive, at 42.

In still other embodiments, the in-beam dose may be greater than about 40 Gy. It is noted that the earlier studies, described supra, on the tissue-sparing effect of synchrotron-generated x-ray microbeams having a thickness in a range of between 0.02 mm to 0.68 mm, were performed using normal, healthy rats. In the studies on healthy spinal cord of rats, it was shown that high dose 0.27-mm microbeams of 750 Gy can ablate thin bands of oligodendrocytes, astrocytes, and oligodendrocyte precursor cells (OPCs) in their direct paths and can also destroy myelin in the irradiated bands. These irradiations were, however, shown to be tolerated by the tissue as a whole and did not cause any observed long-term damage to the tissue's microvasculature. Based on these studies using normal, healthy rats, it was hypothesized that both normal myelin as well as "incomplete," "low quality" myelin could be ablated by the individual microbeams and that new normal myelin would replace the "old myelin" (including incomplete or low-quality myelin) after ablation. Such incomplete, low quality myelin is often produced, for example, by the CNS of a multiple sclerosis (MS) patient as a consequence of the body's natural repeated remyelination attempts that occur after MS attacks, when these attacks are too close together to allow the production of complete or high-quality myelin.

It was also shown in these prior experiments that transaxial irradiation of the normal spinal cord in normal rats caused substantial white-matter demyelination in two weeks, which was followed by nearly full remyelination in three months. Furthermore, it was observed, from images of the irradiated tissue by neurofilament staining after treatment, that the axons were not substantially affected. The lack of significant damage to the axons was also clear from the fact that the rats walked quite normally during the few months after the irradiation.

The observed remyelination was attributed to the regeneration of the glial system from progenitor glial cells, PGCs (or oligodendrocyte precursor cells, OPCs). In that process, it is believed that ablation of OPCs broke the contact inhibition between them and the myelin. As a result, the OPCs proliferated, filled the 0.27-mm cell void (and myelin void) produced by the exposure, differentiated, and began immediately producing new functioning oligodendrocytes. Three months later, full remyelination of the 0.27-mm CNS band was observed. In addition, as noted in other experiments described supra, experimental evidence suggests that high-dose microbeam irradiation can ablate mature oligodendrocytes and astrocytes without damaging the microvasculature, which is the tissue's infrastructure.

Referring again to FIG. 1, at 44, embodiments of the method of irradiating at least a portion 32 of damaged peripheral nerves 30 at in-beam doses sufficient to initiate demyelination, at 12, followed by remyelination, include providing in-beam dose sufficient to ablate myelin and schwann cells, at 44, of the damaged peripheral nerve, wherein bands of old schwann cells and damaged myelin are ablated to make space for new myelin.

Referring to FIGS. 1 and 3, in further embodiments of the method 10, including any suitable characteristics and combinations of in-beam dose and/or dimensions of the microbeams and array as disclosed and described herein, including, but not limited to the examples of characteristics shown, at 45, remyelination may be enhanced by additionally administering schwann cell progenitors (SCP), at 46, to the portion 32 of the damaged peripheral nerve 30 irradiated with the array of microbeams 16. The addition of SCPs, which are often not in abundant supply in the PNS, may stimulate production of new myelin in the damaged peripheral nerve.

In some embodiments, at 50, the SCPs may be administered within one (1) hour after a session of irradiation, at 12, and may, in further embodiments, be administered within a few minutes thereafter.

In other or additional embodiments, at 48, the SCPs may be administered immediately prior, preferably within a few minutes, or in embodiments, up to an hour prior to the irradiating step, at 12.

While the SCPs may be administered to the irradiated portion 32, in embodiments, the SCPs may additionally, or alternatively, be administered, at 52, to peripheral nerve tissue neighboring the irradiated portion 32, either prior to, or after the irradiating step at 12. This will insure a larger population of schwann cell precursors on hand at the time of irradiation.

For any of the embodiments of the method 10 including administering SCPs, at 46, any suitable source can be the source of the schwann cell precursors, both human and other animals. For example, at 54, the SCPs may be adult rat olfactory sphere cells, or neural stem cells from, for example, mice, rats, and/or humans.

In embodiments including ablating, at 44, the myelin and "old" schwann cells to make space for the new myelin, and further administering schwann cell precursors to and/or around the irradiated site, the inviting environment produced by the microbeam irradiation may activate the administered SCPs to fill the voids produced by the microbeam exposures, settle down in those tissue bands, differentiate, make new schwann cells, and remyelinate the tissues. In this way, the administered SPCs, can establish their position in the irradiated tissue, differentiate into mature schwann cells, and produce new myelin.

In further embodiments of the methods 10 of FIG. 1, the irradiating step, at 12, and optionally, in embodiments, the administering step, at 46, can be performed in a number of treatment sessions, at 56, each treatment session being separated by a predetermined period of time.

In further embodiments, the number of treatment sessions is a number sufficient to produce full remyelination. In certain embodiments, the treatment sessions may be repeated multiple times in the course of several days, weeks, or months to produce full remyelination.

The predetermined period of time between each treatment session, at 58, is sufficient, in some embodiments, to allow a second demyelination to occur between each treatment session.

Figure 4:
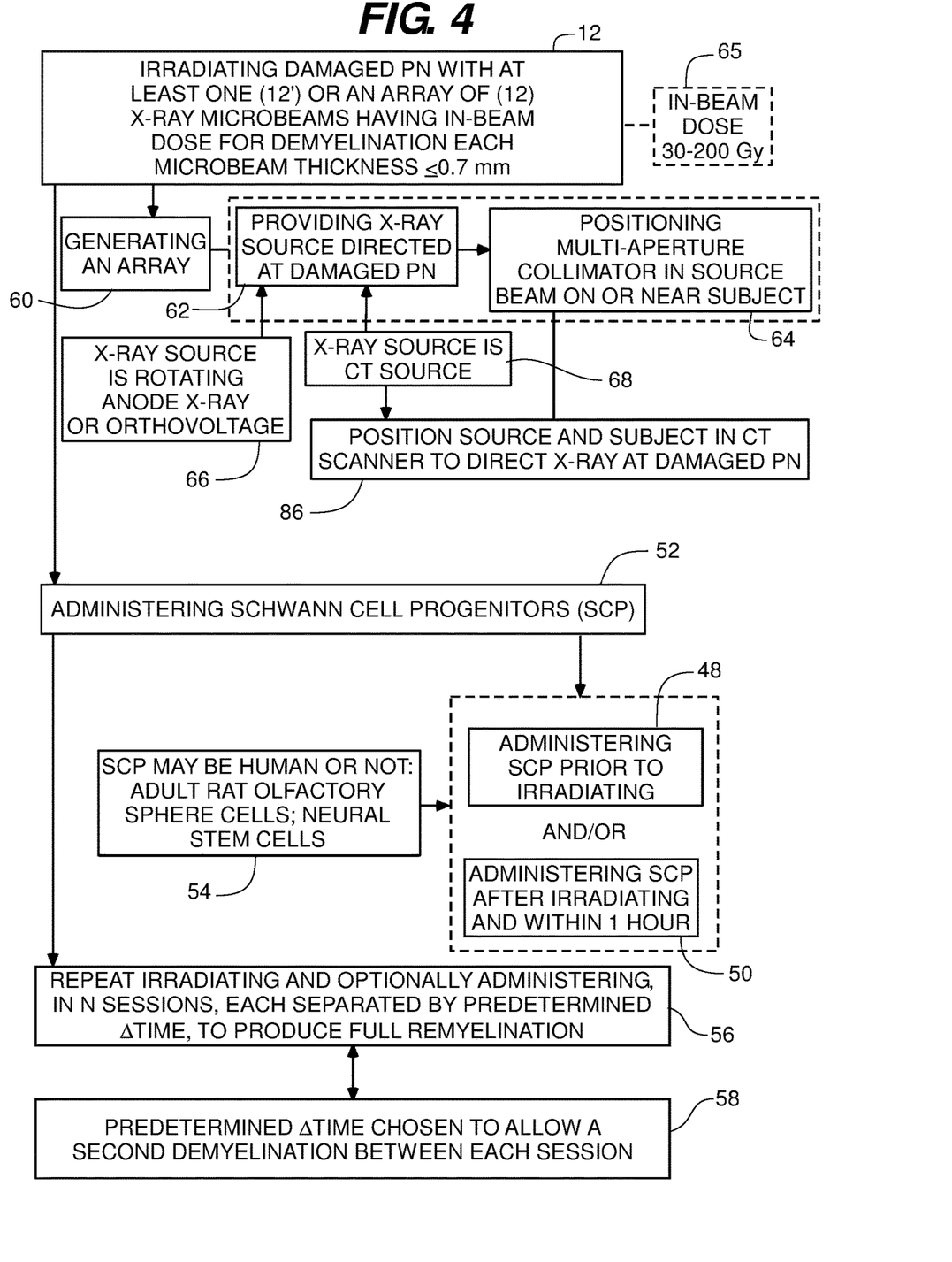
FIG. 4 represents additional embodiments of methods for treating peripheral nerve damage of a subject with microbeam x-ray irradiation.

Referring to FIG. 4, in further embodiments of the methods 10, the irradiating step 12, may further include providing an array of x-ray microbeams, which, in embodiments, may be an array of parallel planar x-ray microbeams, at 60, which may further include providing an x-ray source directed at the portion of the damaged peripheral nerve, at 62, and positioning a multi-aperture collimator, which in embodiments for generating planar microbeams is a multi-slit collimator, at 64, downstream and within a trajectory of the x-ray source, and near or on the subject to generate the array of x-ray microbeams.

It is also noted that for any of the embodiments of FIGS. 1 and 4, the in-beam dose, at 65, may be in a range of between 30-200 Gy inclusive. In addition, in any of the embodiments described in reference to FIG. 4, any combination of the characteristics of the x-ray microbeams disclosed and described herein, including but not limited to the examples provided at 45 in FIG. 1, for example, may be chosen as appropriate.

In some embodiments, the x-ray source provided, at 66, is a rotating anode x-ray tube or an orthovoltage tube.

Any suitable multi-aperture collimator known in the art may be used which is properly dimensioned to generate the array of microbeams of the present disclosure, using the x-ray source provided, at 68, as further described below.

Figure 5:
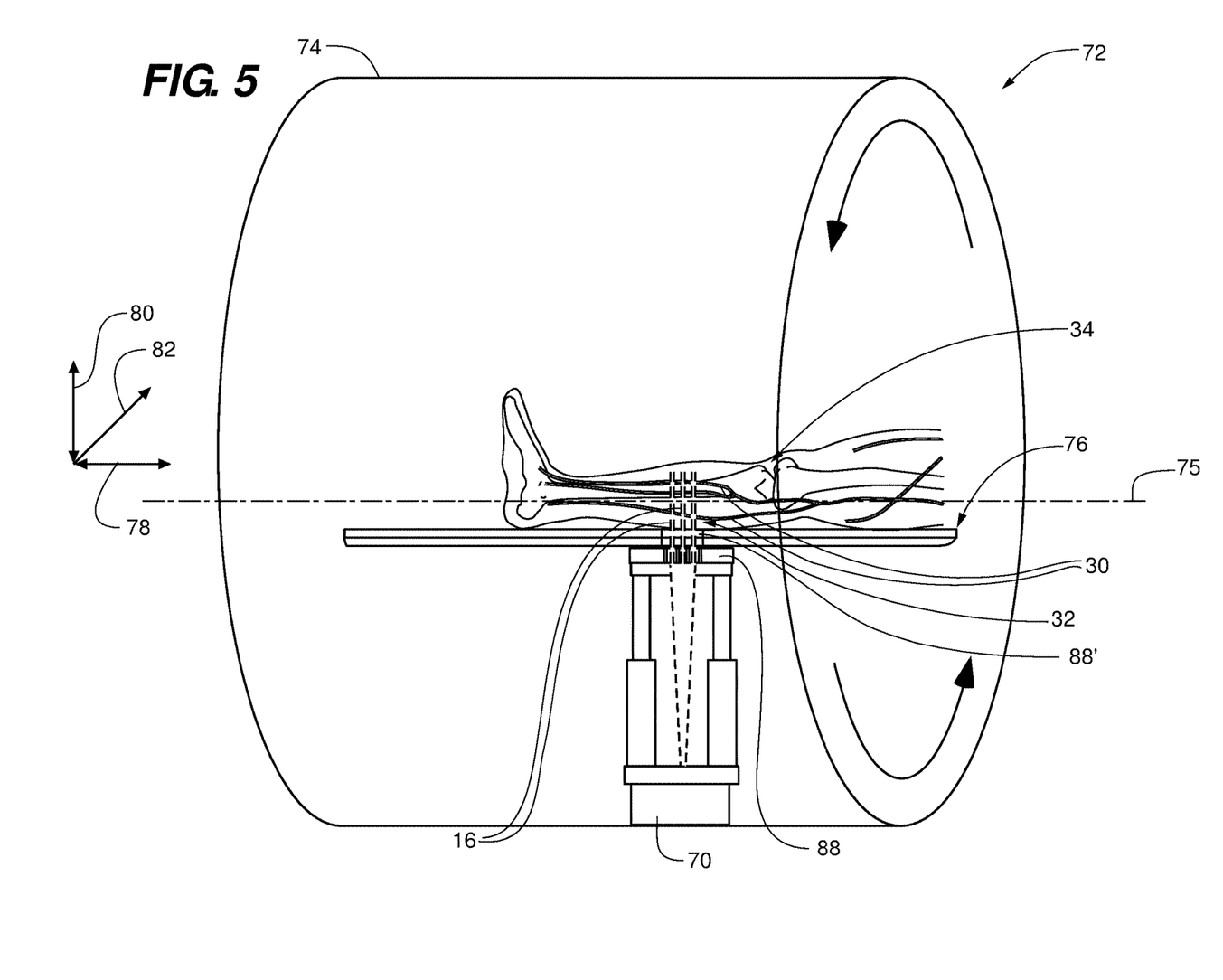
FIG. 5 represents an embodiment of an x-ray source of a computed tomography (CT) scanner for implementing embodiments of the methods of the present disclosure.

With further reference to FIG. 5, in further embodiments, the x-ray source provided, at 68, is an x-ray source 70 of a CT scanner 72. A suitable CT scanner 72 and system is described, for example, in co-owned international patent application, Ser. No. PCT/US18/59401, by Dilmanian et al., ("Dilmanian application"), having an international filing date of Nov. 6, 2018, the entirety of which is incorporated herein by reference thereto. The CT scanner 72 is equipped with a gantry 74, which can be used to rotate around its axis of rotation 75 to position the x-ray source 70, for example, under a bed 76 on which a subject is positioned. In the present embodiments, the peripheral nerve(s) to be irradiated, at 12, will generally not be, although in embodiments they may be, centered along the centrally located axis of the bed of a typical CT scanner. However, as described in the Dilmanian application, for example, in addition to being able to move in and out of the scanner 74 along the horizontal direction 78, in embodiments, the bed 76 of the CT scanner 72 may also be positioned vertically 80 as well as laterally 82 to the gantry's axis of rotation 75, so that portions 32 of damaged peripheral nerves 30, for example, of a subject's leg 34, which are located away from the body's midline or central median plane, can be irradiated, at 12, for treatment with the array of microbeams 16.

Accordingly, referring to FIGS. 4 and 5, methods of the present disclosure including generating the array, at 60, using the x-ray source 70 of a CT scanner 72, at 68, may also include positioning, at 86, both the source 70, e.g., via rotation of the gantry 74, and the subject (e.g., via positioning of the bed 76), so that the x-ray source 70 is directed toward the portion 32 of damaged peripheral nerve to be irradiated.

The method, referring to FIG. 4, may also include positioning a multi-aperture collimator, e.g., a multi-slit collimator 88 on or near the subject, at 64, and in the trajectory of the x-ray source 70. For example, the multi-aperture collimator 88 can be mounted with the x-ray source 70 to rotate together with the x-ray source 70 on the gantry 74, as shown in FIG. 5, and as further described in the Dilmanian application.

Referring to FIG. 5, in embodiments, the multi-aperture collimator 88' may be positioned near or on the subject, at 64, by fixing it into the bed 76 itself, as also described in the Dilmanian application. For example, the bed 76 may include slots on the side of the bed 76, or at an end of the bed 76, into which the multi-aperture collimator 88' can be inserted and positioned where needed to align it in the trajectory of the x-ray source 70, and to irradiate the damaged peripheral nerves with the microbeams 16. In other embodiments, the multi-aperture collimator 88 may be mounted within the trajectory of the x-ray source 70 by mounting it to the x-ray source 70, or to the gantry 74 itself, and held in position as close as possible, and in embodiments, in contact with the subject. In further embodiments using a CT source of a CT scanner 72, as described in reference to FIG. 5, the multi-aperture collimator is a multi-slit collimator for generating planar microbeams. In embodiments, the microbeams 16 may be aligned perpendicular to the axis of rotation 75 as shown in FIG. 5. In various embodiments using a CT scanner 72, by rotating the collimator 88, 88', the planar microbeams 16 may alternatively be aligned parallel to the axis of rotation. By way of illustration, referring to FIG. 2A, if the axis of rotation is disposed along an axis 75' relative to the planes of the microbeams 16 shown in FIG. 2A, then the microbeams are aligned parallel to the axis of rotation.

Referring again to FIG. 4, while the methods described supra use an array of microbeams to treat damaged peripheral nerves, in further embodiments, the irradiating step, at 12', may include irradiating at least a portion of the damaged peripheral nerves with at least one x-ray microbeam to initiate demyelination in the damaged peripheral nerves. In particular embodiments, the irradiating step uses a single microbeam.

The methods may further include the irradiating step, at 12', using at least one microbeam, and administering schwann cell progenitors, which may be, e.g., adult rat olfactory stem cells or neural stem cells, at 54, to at least the portion of the damaged peripheral nerves irradiated with the at least one microbeam, at 52. The administering step may be performed, at 48, prior to the irradiating step 12', and/or after the irradiating step, and in certain embodiments, within 1 hour, at 50 after the irradiating step 12'. It is noted that when the at least one x-ray microbeam, at 12', is an array of x-ray microbeams, the methods herein include the irradiating step, at 12.

While the invention has been shown and described with reference to certain embodiments of the present invention thereof, it will be understood by those skilled in the art that various changes in form and details may be made therein without departing from the spirit and scope of the present invention and equivalents thereof.

What is claimed is:

1. A method for treating a damaged peripheral nerve of a subject, the method comprising:
   irradiating at least a portion of the damaged peripheral nerve with an array of x-ray microbeams having an in-beam dose sufficient to initiate demyelination in the damaged peripheral nerve, wherein each of the microbeams in the array is no greater than 0.7 mm in thickness.

2. The method of claim 1, further comprising:
   administering schwann cell progenitors to at least the portion of the damaged peripheral nerve irradiated with the array, thereby stimulating production of new myelin in the damaged peripheral nerve.

3. The method of claim 2, further including administering schwann cell progenitors to neighboring tissue to the at least the portion.

4. The method of claim 3, wherein the administering step is performed prior to the irradiating step.

5. The method of claim 2, wherein the administering step is performed within an hour after the irradiating step.

6. The method of claim 2, wherein the schwann cell progenitors originate from an animal other than a human.

7. The method of claim 6, wherein the schwann cell progenitors are adult rat olfactory sphere cells.

8. The method of claim 2, wherein the schwann cell progenitors are neural stem cells.

9. The method of claim 2, further comprising repeating each of the steps of irradiating the portion and administering the schwann cell progenitors in a number of treatment sessions, each treatment session being separated by a predetermined period of time, wherein the number of treatment sessions is a number sufficient to produce full remyelination.

10. The method of claim 9, wherein the predetermined period of time between each treatment session is sufficient to allow a second demyelination to occur between each treatment session.

11. The method of claim 1, wherein the thickness of each of the microbeams in the array is between about 0.2 mm and about 0.5 mm inclusive and a spacing on-center between adjacent microbeams in the array is between about 0.7 mm and about 2.0 mm inclusive.

12. The method of claim 1, wherein a gap of at least 0.05 mm is maintained between adjacent microbeams over the portion irradiated.

13. The method of claim 1, wherein the array of microbeams is an array of substantially parallel planar microbeams.

14. The method of claim 1, wherein in-beam doses are at least 100 Gy.

15. The method of claim 1, wherein in-beam doses are at least 30 Gy.

16. The method of claim 1, wherein the in-beam dose is sufficient to ablate myelin of the damaged peripheral nerve, the method including ablating bands of old schwann cells and damaged myelin, thereby making space for new myelin.

17. The method of claim 1, the method including providing the array of x-ray microbeams, including providing an x-ray source directed at the portion of the damaged peripheral nerve and positioning a multi-aperture collimator downstream of the x-ray source and near or on the subject to generate the array of x-ray microbeams.

18. The method of claim 17, wherein the x-ray source includes one of a rotating anode x-ray tube and an orthovoltage x-ray tube.

19. The method of claim 17, wherein the x-ray source is an x-ray tube of a computed tomography (CT) scanner, the method further including providing the computed tomography scanner and positioning the subject and the x-ray source in the computed tomography scanner such that the x-ray source is directed at the portion of the damaged peripheral nerve, the multi-aperture collimator being positioned near or on the subject to generate the array of x-ray microbeams.

20. A method for treating a damaged peripheral nerve of a subject, the method comprising:
irradiating at least a portion of the damaged peripheral nerve with at least one x-ray microbeam to initiate demyelination in the damaged peripheral nerve, the at least one microbeam delivering an in-beam dose of at least 30 Gy, and wherein the at least one microbeam is no greater than 0.7 mm in thickness.

21. The method of claim 20, further comprising administering schwann cell progenitors to at least the portion of the damaged peripheral nerve irradiated with the at least one microbeam, thereby stimulating production of new myelin in the damaged peripheral nerve.

22. The method of claim 21, wherein the administering step is performed prior to the irradiating step.

23. The method of claim 21, wherein the administering step is performed within an hour after the irradiating step.

24. The method of claim 21, wherein the schwann cell progenitors are adult rat olfactory sphere cells.

25. The method of claim 21, wherein the schwann cell progenitors are neural stem cells.

26. The method of claim 21, wherein the x-ray source includes one of a rotating anode x-ray tube and an orthovoltage x-ray tube.

27. The method of claim 20, wherein the at least one x-ray microbeam is an array of x-ray microbeams, the method including providing the array of x-ray microbeams, including providing an x-ray source directed at the portion of the damaged peripheral nerve and positioning a multi-aperture collimator downstream of the x-ray source and near or on the subject to generate the array of x-ray microbeams.

28. The method of claim 27, wherein the x-ray source is an x-ray tube of a computed tomography (CT) scanner, the method further including providing the computed tomography scanner and positioning the subject and the x-ray source in the computed tomography scanner such that the x-ray source is directed at the portion of the damaged peripheral nerve.

29. The method of claim 27, wherein a gap of at least 0.05 mm is maintained between adjacent microbeams over the portion irradiated.

30. The method of claim 27, wherein the array of microbeams is an array of substantially parallel planar microbeams.

* * * * *